US00PP24849P2

(12) United States Plant Patent
Kordes

(10) Patent No.: US PP24,849 P2
(45) Date of Patent: Sep. 9, 2014

(54) SHRUB ROSE PLANT NAMED 'KORBLIXMU'

(50) Latin Name: *Rosa hybrida*
Varietal Denomination: KORblixmu

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 54 days.

(21) Appl. No.: 13/573,185

(22) Filed: Aug. 28, 2012

(51) Int. Cl.
*A01H 5/00* (2006.01)

(52) U.S. Cl.
USPC ..... Plt./103; Plt./101; Plt./102

(58) Field of Classification Search
USPC ..... Plt./101, 102, 103
See application file for complete search history.

(56) References Cited

PUBLICATIONS

"The Capital Rose" newsletter—publication of the Arlington Rose Foundation and the Potomac Rose Society, Oct. 2007,(8 pages total).*

Packing slip showing first comercial sale of 'KORblixmu' 'Newflora, LLC' invoice Jan. 15, 2014 for 'KORblixmu'.

* cited by examiner

*Primary Examiner* — Susan McCormick Ewoldt

(57) ABSTRACT

A new and distinct variety of rose with long lasting, novel white flowers, and attractive foliage with excellent disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORblixmu'. The new variety of rose plant of the present invention originated from a controlled crossing in a breeding program of two distinct parents during the summer of 1998. The crossing was between an 'un-named seedling', the seed parent, and another 'un-named seedling', the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORblixmu'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. 'KORblixmu' has cupped, medium sized flowers, whereas the 'un-named seedling' has pointed, large sized flowers.
2. 'KORblixmu' has better disease resistance than the 'un-named seedling'.

The new rose plant may be distinguished from its pollen parent, an 'un-named seedling', by the following combination of characteristics:

1. 'KORblixmu' has medium sized white flowers, whereas the 'un-named seedling' has small yellow flowers.
2. The flowers of 'KORblixmu' have a semi-double petal count, whereas the flowers of the 'un-named seedling' have a single petal count.

The objective of the hybridization was to create a new and distinct rose plant with unique qualities, such as:

1. Uniform growth and flowering;
2. Abundant attractive, recurrent white flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORblixmu' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORblixmu' was selected in May, 1999 from the seedling beds to be asexually propagated for further evaluation. The first asexual propagation of 'KORblixmu' was done by budding to seedling understocks in July, 1999 at the inventor's nursery in Offenseth-Sparrieshoop, Germany.

This initial and other subsequent propagations conducted in controlled environments demonstrate that 'KORblixmu' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORblixmu'.

DETAILED BOTANICAL DESCRIPTION

The following is a description of 'KORblixmu', as observed growing in July, 2012 in a nursery in Jackson County, Oreg. on plants of 1 years of age. Color references are made using The Royal Horticultural Society (London, England) Colour Chart, 2001 except where common terms of color are used.

For a comparison, several physical characteristics of the rose variety 'KORquelda', a rose variety from the same inventor described and illustrated in U.S. Plant Pat. No. 17,048 and issued on Aug. 22, 2006 are compared to 'KORblixmu' in Chart 1.

CHART 1

| Characteristic | 'KORblixmu' | 'KORquelda' |
|---|---|---|
| Bud color, as sepals first unfold | White Group 155D | Green-Yellow Group 1B |
| Shape of flower upon opening, lower part | Flat | Convex |
| Number of pistils | 40 | 80-85 |

Parents:

*Seed parent*.—An 'un-named seedling'.

*Pollen parent*.—An 'un-named seedling'.

Classification:

*Botanical classification*.—*Rosa hybrida* 'KORblixmu'.

*Commercial classification*.—Shrub rose.

FLOWER AND FLOWER BUD

*Blooming habit*.—Recurrent.

*Flower bud*.—Size: Upon opening, 25 mm in length from base of receptacle to distal end of bud and 10 mm diameter at its widest point. Bud form: Short. Pointed ovoid. Bud color: As sepals first unfold, bud color is White Group 155D. When ¼ open, the upper surface of petals is White Group 155B, and the lower surface is White Group 155D. Sepals: Color: Upper surface: Yellow-Green Group 146C. Lower surface: Yellow-Green Group 146C. Intonations of Greyed-Purple Group 185B found on the lower side, and occasionally on the upper side, of the midsection. Size: Average 20 mm (l)×7.5 mm (w). Shape: Moderate foliaceous appendages on three of the five sepals. Apex: Cirrose. Base: Flat at union with receptacle. Quantity: Five. Surface texture: Upper side: Pubescent. Lower surface: Lightly Pubescent. Margins: Pubescent.

*Receptacle*.—Surface: Smooth. Color: Yellow-Green Group 144A. Shape: Urn-shaped. Size: 6 mm (h)×8 mm (w).

*Pedicel*.—Surface: With fine hairs. Length: 60 to 80 mm average length. Diameter: 4 to 5 mm average diameter. Color: Yellow-Green Group 146C, with intonations of Greyed-Orange Group 175A. Strength: Strong. Borne: Multiple flower buds per stem, generally 4 to 8.

Flower bloom:

*Fragrance*.—Light.

*Duration*.—On the plant 3 to 5 days. Long lasting. As a cut flower, 2 to 3 days. Senesced petals drop away cleanly.

*Size*.—Medium for a shrub rose. When open, the average flower diameter is 50 mm and the average flower height is 30 mm.

*Form*.—Shape of flower when viewed from the side: Upon opening, upper part: Flattened convex. Upon opening, lower part: Flat. Open flower, upper part: Flattened convex. Open flower, lower part: Concave.

Color:

*Upon opening, petals*.—Outermost petals: Outer Side: White Group 155D. Inner Side: White Group 155B. Innermost petals: Outer Side: White Group 155D. Inner Side: White Group 155D, with a basal zone of Yellow Group 2D.

*Upon opening, basal petal spots*.—Basal petal spot, outermost petals: Outer Side: None. Inner Side: Yellow Group 2D. Basal petal spot, innermost petals: Outer Side: Yellow Group 2C. Inner Side: Yellow Group 2C.

*After opening, petals*.—Outermost petals: Outer Side: White Group 155D. Inner Side: White Group 155C. Innermost petals: Outer Side: White Group 155B. Inner Side: White Group 155B.

*After opening, basal petal spots*.—Basal petal spot, outermost petals: Outer Side: White Group 155C. Inner Side: Greyed-Yellow Group 160B. Basal petal spot, innermost petals: Outer Side: Green-Yellow Group 1C. Inner Side Green-Yellow Group 1C.

General tonality: On open flower: White Group 155C. No change in the general tonality at the end of the third day. Afterwards, general tonality is White Group 155C.

Petals:

*Petal count*.—Double.

*Average range*.—Approximately 35-40 petals under normal conditions.

*Petal reflex*.—Petals reflex slightly.

*Petal edge*.—Entire.

*Petal shape*.—Obovate. Apex shape is obtuse. Shape of base is obtuse.

*Petal size*.—25 mm (l)×20 mm (w).

*Thickness*.—Thin.

*Petal arrangement*.—Not formal.

Petaloids:

*Petaloid count*.—Average of 0-3 per flower.

*Petaloid size*.—20 mm (l)×5 mm (w).

*Petaloid color*.—Color of inner side is Yellow Group 2D. Color of outer side is Yellow Group 2D.

*Petaloid texture*.—Thin.

*Margins*.—Undulated.

*Petaloid shape*.—Most commonly spatulate, with some petaloids highly irregular. Apex: Obtuse. Base: Attenuate.

Reproductive organs:

*Pistils*.—Abundant. Approximately 40 present. Stigmas: Location: Slightly inferior in position to anthers. Color: Greyed-Yellow Group 160A. Styles: Length: About 4 mm long. Color: Yellow-Green Group 145B, with intonations of Red Group 44C on the upper end of the style.

*Stamens*.—Approximately 50 on average and regularly arranged. Anthers: Size: Average 2 mm (l)×1 mm (w).

Pollen: Generally present. Color: Greyed-Orange Group 167A. Filaments: Color: Yellow-Green Group 154B. Length: 5 mm.

THE PLANT

*Growth*.—Moderate.

*Plant habit*.—Upright to bushy habit. When grown as a budded field plant, the average plant height is 120 cm and the average plant width is 100 cm.

*Blooming*.—Fioriferous.

*Stems*.—Stem color: Young wood: Yellow-Green Group 145A, with intonations of Greyed-Red Group 182B. Older wood: Yellow-Green Group 146C. Stem surface: Young wood: Smooth. Older wood: Smooth.

*Prickles*.—Present. Incidence: Average of 8 per each 10 cm of stem. Size: Average length: 10 mm. Color: Immature prickles: Greyed-Yellow Group 161A. Mature prickles: Greyed-Yellow Group 161B. Shape: Concave. Anthocyanin: Greyed-Red Group 180B.

*Leaves and leaflets*.—Normally 5 leaflets on normal leaves in middle of the stem. Venation pattern: Pyramidal net pattern. Leaf size: 140 mm (l)×110 mm (w). Abundance: Average. Texture: Thick. Upper side of leaflet: Semi-glossy. Smooth. Under side of leaflet: Matte. Rough. Color, mature foliage: Upper Leaf Surface: Green Group 137B. Lower Leaf Surface: Yellow-Green Group 146B. Color, juvenile foliage: Upper Leaf Surface: Green Group 137A. Lower Leaf Surface: Yellow-Green Group 146B. Intonations of Greyed-Orange Group 175A present on margins.

*Stipules*.—Size: 25 mm long, 5 mm from distal tip to distal tip. Stipule color: Yellow-Green Group 146B. Margins: With abundant stipitate glands. Shape: Apex: Apiculate. Base: Flat.

*Petiole*.—Length: Average 30-40 mm. Diameter: Average 3 mm. Petiole color: Yellow-Green Group 146B. Underneath: Yellow-Green Group 146C. Margins: Limited numbers of stipitate glands. Prickles: With limited numbers of prickles.

*Petiole rachis*.—Length: Average 25 mm. Diameter: Average 2 mm. Color: Yellow-Green Group 146D. Margins: With limited numbers of stipitate glands. Prickles: A few small prickles underneath.

*Leaflets*.—Size: Average size of the terminal leaflet is 65 mm (l)×40 mm (w). Shape: Ovate. Base: Obtuse. Apex: Acute. Margins: Finely serrated. Surface: Upper: Semi-glossy. Lower: Matte. Texture: Thick. Arrangement: Odd pinnate. Venation Reticulate.

Hips/seed formation: None observed.

Winter hardiness: To date, the variety has been grown successfully in Zones 5-9.

Disease resistance: Exceptional resistance to Powdery mildew (*Sphaerotheca pannosa*) and blackspot (*Diplocarpon rosae*) diseases under normal growing conditions.

I claim:

1. A new and distinct variety of rose plant, as described and illustrated herein.

* * * * *

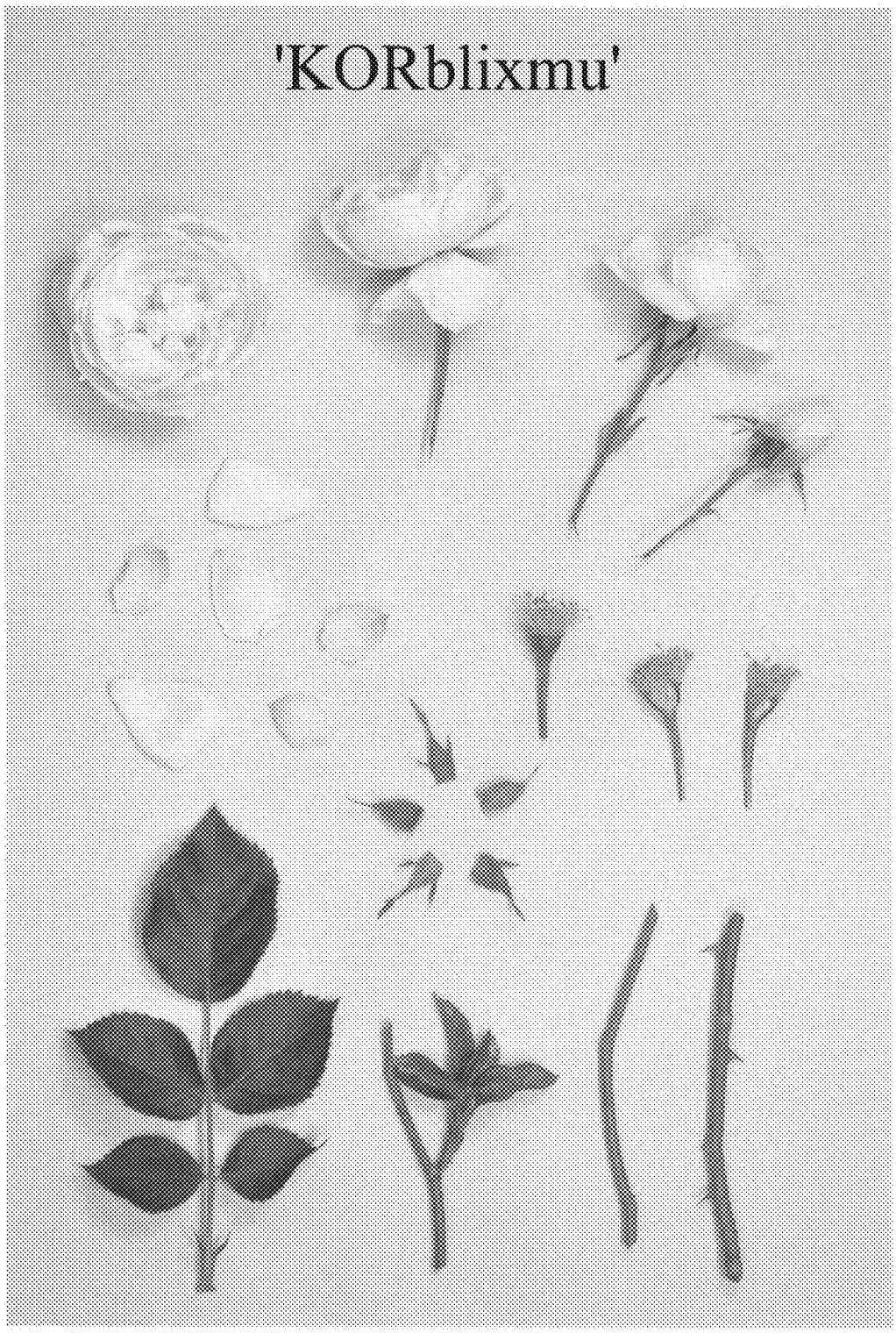
'KORblixmu'